United States Patent [19]

Schobel et al.

[11] Patent Number: 5,093,387
[45] Date of Patent: Mar. 3, 1992

[54] DENTURE ADHESIVE

[75] Inventors: Alexander M. Schobel, Whitehouse Station; Lori D. Kumar, Princeton, both of N.J.

[73] Assignee: Warner-Lambert Company, Morris Plains, N.J.

[21] Appl. No.: 454,671

[22] Filed: Dec. 21, 1989

[51] Int. Cl.$^5$ .................. A61K 6/00; A61K 7/16; C08L 89/00
[52] U.S. Cl. ................. 523/120; 524/45; 524/55; 524/492; 424/49
[58] Field of Search ........... 523/120; 524/45, 492, 524/55; 424/49

[56] References Cited

U.S. PATENT DOCUMENTS

| | | | |
|---|---|---|---|
| 3,868,339 | 2/1975 | Keegan et al. | 523/120 |
| 4,746,690 | 5/1988 | Busch et al | 524/55 |
| 5,006,571 | 4/1991 | Kumar et al. | 523/120 |

Primary Examiner—Nathan M. Nutter
Attorney, Agent, or Firm—Charles A. Gaglia, Jr.

[57] ABSTRACT

A denture adhesive base composition comprises a substantially anhydrous mixture of a cationic derivatives of guar gum, a mixed Na/Ca salt of methyl vinyl ether-maleic anhydride and sodium carboxymethylcellulose. A denture adhesive composition including this base composition is provided, as well as a method for formulating the novel adhesives of the invention. Upon hydration, the denture adhesives of the invention form denture adhesive compositions exhibiting improved denture holding and adhesive duration properties.

25 Claims, No Drawings

DENTURE ADHESIVE

BACKGROUND OF THE INVENTION

1. Field of the Invention

This invention relates to denture adhesives or stabilizers, and particularly to an improved anhydrous denture adhesive composition.

2. Description of the Prior Art

Traditionally, adherent powders used to secure dentures within the mouth were prepared from such materials as finely powdered natural gums, i.e. karaya, acacia or tragacanth gum. These materials have the particular property of swelling to many times their original volume upon the addition of water to form a gelatinous or mucilaginous mass. Denture adhesive powders may be a combination of one or more natural gums, generally flavored with pleasant tasting volatile oils. Many other additives may also be included, such as antiseptics, stabilizers, bacteriocides, special deodorants, plasticizing agents, fillers, coloring agents, and the like.

Cream forms of the denture adherent, prepared from finely ground particles of the natural gums dispersed in a cream base, are also available and may be used instead of the powder compositions. In any event, when wet with water, the natural gum in either the cream or powder formulation expands to become a viscous gel which acts as a cushion and an adherent between the denture plate and the gum tissue.

While these relatively simple formulations are effective in securing dentures within the oral cavity for a short period of time, generally more than one application of adhesive per day is necessary. This is, at best, inconvenient and therefore, most undesirable.

In recent years, there have been numerous improvements in the above-described simple denture adhesive formulations. For example, U.S. Pat. No. 3,736,274 discloses a denture adhesive containing three essential ingredients: a maleic anhydride and/or acid copolymer (with a lower alkyl vinyl ether), a polymeric N-vinyl lactam, and sodium carboxymethylcellulose, preferably incorporated into a diluent such as petrolatum and/or mineral oil.

U.S. Pat. No. 4,280,936 discloses a denture adhesive comprising sodium carboxymethylcellulose and poly (ethylene oxide) homopolymer in a mineral oil base.

U.S. Pat. No. 4,514,528 is directed to a hydrophilic denture adhesive which consists of an admixture of mixed, partial salts of lower alkyl vinyl ether-maleic anhydride-type copolymers with either sodium carboxymethylcellulose or poly (ethylene oxide) homopolymer or both in a hydrophilic vehicle.

U.S. Pat. No. 4,518,721 discloses a denture adhesive which consists of sodium carboxymethylcellulose and poly (ethylene oxide) in a hydrophilic vehicle comprising certain polyethylene glycols and, optionally, glycerin.

U.S. Pat. No. 4,569,955 discloses a denture adhesive containing an adhesive polymeric fraction comprising an admixture of mixed, partial salts of lower alkyl vinyl ether-maleic anhydride-type copolymers with sodium carboxymethylcellulose in a mineral oil vehicle thickened with polyethylene having a molecular weight of 1,000 to 21,000.

While all of the above denture adhesives provide some improvement over simple formulations containing only finely powdered natural gums, it is generally recognized that no one product has yet been developed which can accommodate over a long period of time, the many variations in temperatures, pH and mechanical agitation which are quite normal in the oral cavity.

It has now been found that the denture adhesive of this invention will provide superior adhesive duration and holding properties over prolonged periods of time and under unusally varied conditions, without the disadvantages characteristic of previously known products.

SUMMARY OF THE INVENTION

The novel denture stabilizers formed according to the present invention are generally prepared by mixing a denture adhesive base composition with additional materials to produce denture adhesive compositions which, whether formulated in powder or paste form, exhibit excellent properties as denture stabilizers.

Applicant has unexpectedly discovered a denture adhesive base composition comprising a substantially anhydrous mixture of a cationic derivative of guar gum, a mixed Na/Ca salt of methyl vinyl ether-maleic anhydride and sodium carboxymethylcellulose.

In one preferred embodiment of the invention, it has been unexpectedly discovered to form a denture adhesive composition which comprises a substantially anhydrous mixture of from about 40 to about 60 percent by weight, based on the total weight of the denture adhesive composition, of a denture adhesive base composition containing a cationic derivative of guar gum, a mixed Na/Ca salt of methyl vinyl ether-maleic anhydride and sodium carboxymethylcellulose.

In another preferred embodiment, it has been unexpectedly discovered to form a denture adhesive composition comprising a substantially anhydrous mixture of:
a) from about 40 to about 60 percent by weight, based on the total weight of the denture adhesive composition, of a denture adhesive base composition containing a cationic derivative of guar gum, a mixed Na/Ca salt of methyl vinyl ether-maleic anhydride and sodium carboxymethyl-cellulose; and
b) from about 40 to about 60 percent by weight, based on the total weight of the denture adhesive composition, of additional materials selected from the group consisting of waxes, oils, preservatives, flavoring agents, colorants, sweetening agents, viscosity modifiers and mixtures thereof.

In an especially preferred embodiment it has been unexpectedly discovered to form a denture adhesive composition comprising a substantially anhydrous mixture of:
a) from about 10.0 to about 20 percent by weight, based on the total weight of the denture adhesive composition, of a cationic derivative of guar gum;
b) from about 20 to about 30 percent by weight, based on the total weight of the denture adhesive composition, of a mixed Na/Ca salt of methyl vinyl ether-maleic anhydride;
c) from about 10 to about 25 percent by weight, based on the total weight of the denture adhesive composition, of sodium carboxymethylcellulose; and
d) additional materials in an amount sufficient to yield a denture adhesive composition having a total weight equal to 100 percent by weight of the total denture adhesive composition.

The invention also involves a method for preparing these novel denture stabilizers.

In one preferred embodiment, a method for preparing a denture adhesive base composition comprises:
a) preparing a substantially anhydrous mixture of a cationic derivative of guar gum, a mixed Na/Ca salt of methyl vinyl ether-maleic anhydride and sodium carboxymethylcellulose;
b) forming a denture adhesive base composition including said mixture; and
c) recovering said denture adhesive base composition.

DESCRIPTION OF THE INVENTION

Applicant has unexpectedly discovered a novel denture adhesive base composition comprising a substantially anhydrous mixture of a cationic derivative of guar gum, a mixed Na/Ca salt of methyl vinyl ether-maleic anhydride and sodium carboxymethylcellulose.

Denture adhesive compositions formed with the above-described denture adhesive base composition yield a product which provides surprising good performance as a denture stabilizer Specifically, denture adhesives of the present invention require fewer applications per day, exhibit increased holding power, denture cushioning and duration of holding, exhibit reduced oozing properties, and provide greater consumer confidence of product function.

The invention comprises a unique combination of three essential components, namely a cationic derivative of guar gum, a mixed Na/Ca salt of methyl vinyl ether-maleic anhydride and sodium carboxymethylcellulose. In the absence of any of these components from the formulations of this invention, compositions may be prepared which do not exhibit the enhanced effect achieved from this combination.

Guar gum is a commercially available water-soluble plant mucilage obtained from the ground endosperms of Cyanopsis tetragonoloba, cultivated in Pakistan as livestock feed.

The presently disclosed adhesive compositions utilize a commercially available cationic derivative of guar gum which has been unexpectedly found to react with sodium carboxymethylcellulose in the presence of the mixed Na/Ca salt of methyl vinyl ether-maleic anhydride, to form a denture adhesive composition exhibiting enhanced adhesiveness, and particularly enhanced cohesive properties.

A preferred cationic derivative of guar gum which has been found to be useful in preparing the adhesive formulations of the invention is guar gum, 2-hydroxy-3-(trimethyl ammonio)-propyl ether, chloride.

The mixed Na/Ca salt of methyl vinyl ether-maleic anhydride is a commercially available material known in the art. The mixed Na/Ca salt of methyl vinyl ether-maleic anhydride is a hydrophilic long chain polymer which has adhesive properties.

Upon addition of the third component of the invention, sodium carboxymethylcellulose, a denture adhesive is provided, which, upon hydration, forms an adhesive yet extremely cohesive matrix.

Sodium carboxymethylcellulose is a commercially available synthetic gum derived from cellulose, and generally comprises an anionic, water-soluble, long chain polymer. The particle size of the sodium carboxymethylcellulose utilized in the present invention is preferably 60 mesh or smaller.

When these three components are intermixed, a denture adhesive base composition is formed which exhibits superior characteristics as a denture stabilizer when incorporated into a denture adhesive composition. Specifically, denture adhesive compositions formulated with the denture adhesive base composition of the invention exhibit improved denture holding and improved denture adhesive duration properties.

The denture adhesive base composition may comprise from about 12.5 to about 50 percent by weight of a cationic derivative of guar gum, from about 33 to about 75 percent by weight of a mixed Na/Ca salt of methyl vinyl ether-maleic anhydride, and from about 12.5 to about 62 percent by weight of sodium carboxymethylcellulose, based on the total weight of the denture adhesive base composition.

Preferably, the denture adhesive base composition comprises from about 17 to about 27 percent by weight of a cationic derivative of guar gum, from about 43 to about 53 percent by weight of a mixed Na/Ca salt of methyl vinyl ether-maleic anhydride, and from about 17 to about 27 percent by weight of sodium carboxymethylcellulose, based on the total weight of the denture adhesive base composition.

The denture adhesive base compositions are useful to prepare denture adhesive compositions. According to the invention, a denture adhesive composition is provided which comprises a substantially anhydrous mixture of from about 40 to about 60 percent by weight percent, based on the total weight of the denture adhesive composition wherein the denture adhesive base composition contains three essential components, a) a cationic derivative of guar gum, b) mixed Na/Ca salt of methyl vinyl ether-maleic anhydride and c) sodium carboxymethylcellulose.

In addition to the foregoing materials, the denture adhesive composition may be formulated with additional components well known in the denture adhesive art. Such additional materials utilized in the invention may comprise waxes, oils, preservatives, flavoring agents, colorants, sweetening agents, viscosity modifiers and so forth.

The waxes useful in the invention comprise both natural and synthetic waxes and include without limitation animal waxes such as beeswax, lanolin and shellac wax, vegetable waxes such as carnauba, candelilla and bayberry wax, mineral wax such as petroleum waxes including paraffin, and microcrystalline.

The oils useful in the invention include without limitation mineral oil, vegetable oil such as corn, soybean, cottonseed, castor, palm and coconut oils and animal oil such as fish oil, and oleic acid.

Flavoring agents well known to the denture adhesive art may be added to the compositions of the instant invention. These flavoring agents may be chosen from synthetic flavor oils and/or oils derived from plants, leaves, flowers, fruits and so forth, and combinations thereof. Representative flavor oils include: spearmint oil, cinnamon oil, oil of wintergreen (methylsalicylate) and peppermint oils. Also useful are artificial, natural or synthetic fruit flavors such as citrus oil including lemon, orange, grape, lime and grapefruit, and fruit essences including apple, strawberry, cherry, pineapple and so forth. The flavoring agent may be a liquid, spray dried, encapsulated, sorbed on a carrier and mixtures thereof. A preferred flavoring agent is peppermint oil, commercially available from Rose Mitcham. The amount of flavoring agent utilized may vary depending on such factors as flavor type, adhesive formulation and strength desired. In general, amounts of about 0.01% to about 5.0% by weight of the total denture adhesive composition are usable, with amounts of about 0.05% to 0.15% being preferred.

Preservatives which may be used in the denture adhesive formulations of the invention include those known antimicrobial agents conventionally employed in the art, such as benzoic acid and sodium benzoate; the parabens; sorbic acid and sorbates; propionic acid and propionates; acetic acid and acetates; nitrates and nitrites; sulfur dioxide and sulfites; antibiotics; diethyl pyrocarbonate; epoxides; hydrogen peroxide; and phosphates. The parabens include the methyl, ethyl, propyl, and butyl esters of parahydroxybenzoic acid. Methyl paraben and propyl paraben are the preferred preservatives of the invention, preferably utilized in amounts of about 0.03% to about 0.6% by weight of the total denture adhesive composition.

The denture adhesive compositions may also include the use of sweeteners well known in the art.

The sweetening agent may be selected from a wide range of materials including water-soluble agents, water-soluble artificial sweeteners, and dipeptide based sweeteners, including mixtures thereof. Without being limited to particular sweeteners, representative illustrations encompass:

A. Water-soluble sweetening agents such as monosaccharides, disaccharides and polysaccharides such as xylose, ribose, glucose, mannose, galactose, fructose, dextrose, sucrose, sugar, maltose, partially hydrolyzed starch, or corn syrup solids and sugar alcohols such as sorbitol, xylitol, mannitol, maltitol, hydrogenated starch hydrolysate and mixtures thereof.

B. Water-soluble artificial sweeteners such as the soluble saccharin salts, i.e., sodium or calcium saccharin salts, cyclamate salts, acesulfame-K, sucralose and the like, and the free acid form of saccharin.

C. Dipeptide based sweeteners such as L-aspartyl-L-phenylalanine methyl ester and materials described in U.S. Pat. No. 3,491,131, L-D-aspartyl-N-(2,2,4,4-tetramethyl-3-thietanyl-D-alaninamide hydrate) and the like.

In general, the amount of sweetener will vary with the desired amount of sweetener selected for a particular denture adhesive formulation. This amount may be about 0.001% to about 5% by weight of the final denture adhesive composition when using an easily extractable sweetener.

The colorants useful in the present invention include pigments such as titanium dioxide, and may also include dyes suitable for food, drug and cosmetic applications. These colorants are known as F.D. & C. dyes. The materials acceptable for the foregoing spectrum of use are preferably water-soluble. Illustrative examples include indigo dye, known as F.D. & C. Blue No. 2, which is the disodium salt of 5,5,-indigotindi-sulfonic acid. Similarly, the dye known as F.D. & C. Green No. 1, comprises a triphenylmethane dye and is the monosodium salt of the 4-[4-N-ethyl-p-sulfobenzylamino) diphenylmethylene]-[1-N-ethyl-N-P-sulfo-benzyl)-2, 5-cyclohexadienimine]. A preferred colorant is F.D. & C. Red No. 3. A full recitation of F.D. & C. and D. & C. colorants and their corresponding chemical structures may be found in the Kirk-Othmer Encyclopedia of Chemical Technology, 3rd Edition, in Volume 6, at pages 561-595.

The viscosity modifiers useful herein include polyethylene and its derivatives, quaternary ammonium compounds and similar agents, starches, gums and casein gelatin. In general, the viscosity of the present adhesive formulations should be modified such that the final product may be readily extruded. Extrusion characteristics of the present denture adhesives have been determined to be most ideal when the compositions contain less than 60 percent total solids.

Another optional additive useful in the adhesive formulations of the present invention is ethylene oxide polymer. Ethylene oxide polymer is a water-soluble, non-ionic white powder having an average molecular weight of about 100,000 to about 5,000,000. The preferred ethylene oxide polymer optionally utilized in the present invention is commercially available.

Fumed silica is an additional optional additive which may be included in the inventive denture adhesive formulations. Fumed silica is a commercially available colloidal form of silica made by the combustion of silicon tetrachloride.

In another aspect of the invention, a denture adhesive composition is provided which comprises a substantially anhydrous mixture of:

a) from about 40 to about 60 percent by weight, based on the total weight of the denture adhesive composition, of a denture adhesive base composition containing a cationic derivative of guar gum, a mixed Na/Ca salt of methyl vinyl ether-maleic anhydride and sodium carboxymethylcellulose; and b) from about 40 to about 60 percent by weight, based on the total weight of the denture adhesive composition, of additional materials selected from the group consisting of waxes, oils, preservatives, flavoring agents, colorants, sweetening agents, viscosity modifiers and mixtures thereof.

In an especially preferred aspect of the invention, a denture adhesive composition is formed which comprises a substantially anhydrous mixture of:

a) from about 10 to about 20 percent by weight, based on the total weight of the denture adhesive composition, of a cationic derivative of guar gum;

b) from about 20 to about 30 percent by weight, based on the total weight of the denture adhesive composition, of a mixed Na/Ca salt of methyl vinyl ether-maleic anhydride;

c) from about 10 to about 25 percent by weight, based on the total weight of the denture adhesive composition, of sodium carboxymethylcellulose; and d) additional materials in an amount sufficient to yield a denture adhesive composition having a total weight equal to 100 percent by weight of the total denture adhesive composition.

The denture adhesive compositions may be in the form of a paste or powder mixture. The means for preparing such formulations is well known in the denture adhesive art.

In a preferred aspect of the invention, the denture adhesive base composition may further include at least one cream base material selected from the group consisting of petrolatum, natural and synthetic oils and mixtures thereof.

In another preferred aspect of the invention, the denture adhesive base composition may further include a cream base material which is a combination of mineral oil with a minor amount of polyethylene wax having an average molecular weight of 1,000 to 20,000.

In another preferred aspect of the invention, the denture adhesive base composition may further include nontoxic, powdered, excipient materials.

The denture adhesive compositions and denture adhesive base compositions of this invention may be formulated to contain the cationic derivative of guar gum, mixed Na/Ca salt of methyl vinyl ether-maleic anhydride and sodium carboxymethylcellulose in either powder or paste form. In the powder form, the components are admixed with the flavoring agents and colorants, together with other non-essential ingredients such as non-toxic anti-caking agents (silica, magnesium stearate, talcum powder or the like). The mixture of ingredients is thoroughly agitated or stirred to yield a generally homogenous intermixing of all components. In the paste formulations, the cationic derivative of guar gum, mixed Na/Ca salt of methyl vinyl ether-maleic anhydride and sodium carboxymethylcellulose are admixed. With petrolatum, along with the previously described waxes, oils, preservatives, flavoring agents, colorants, sweetening agents, viscosity modifiers and so forth.

A particularly preferred paste or cream formulation is prepared by utilizing as the cream or paste base, the product of U.S. Pat. No. 3,215,599, the disclosure of which is incorporated herein by reference. The cream or paste base of this patent is characterized as a mixture of white petroleum oil with a minor amount of a polyethylene wax having an average molecular weight of 1,000 to 20,000. This product is described as having emollient properties, useful in the formulation of medicaments where absorption of the medicaments by the skin is of paramount importance. Denture adhesive creams formulated with this petroleum oil/polyethylene wax blend as the paste or cream base display unusually good stability, extrudability and product appearance.

The method for preparing the denture adhesive compositions according to the present invention, whether formulated as a powder, paste or cream employs conventional types of mixing equipment which are known in the art for blending, heating and cooling solids and liquids.

The method for preparing the denture adhesive base compositions and denture adhesive compositions containing the same may be conveniently prepared by mixing the components until a homogeneous mixture is obtained and recovering the resulting product. Preferably the base composition is prepared as a preblended formulation which can be mixed with the remaining components used to prepare the final formulation. Mixing is conveniently performed at temperatures suitable to melt the components to be blended. For example, if polyethylene and mineral oil are to be employed such material may be heated to temperatures from about 50° to 110° C., and are preferably cooled prior to blending with the base preblend. Flavoring agents may be added to the preblend and/or the wax/oil mixture prior to mixing in the final mixture.

Whether formulated as a powder, paste or cream, the denture adhesive compositions and base compositions of this invention, when applied to dentures and exposed to moisture, hydrate to form adhesive compositions which exhibit unexpectedly superior characteristics in comparison with denture adhesives of the prior art. Once formulated the compositions may be used or stored for future use.

The following examples are given to illustrate the invention, but are not deemed to be limiting thereof. All percentages given throughout the specification are based on the weight of the final denture adhesive composition unless otherwise indicated and are based on 100% by weight.

EXAMPLE 1

Preparation of a Denture Adhesive Cream following ingredients:

| Ingredients | Percent W/W |
| --- | --- |
| Mineral oil | 19.00 |
| Petrolatum | 20.00 |
| Fumed silica | 1.0 |
| Mixed Na/Ca salt of methyl vinyl ether-maleic anhydride | 28.00 |
| Sodium carboxymethylcellulose | 15.00 |
| Cationic derivative of guar gum | 15.00 |
| Ethylene oxide polymer | 1.85 |
| Methyl paraben | 0.05 |
| Propyl paraben | 0.10 |
| | 100.00 |

A. Weigh mineral oil and petrolatum into a pot, and mix to form a homogenous mixture while raising the temperature to 90°-95° C. Check to assure complete solution. With continued mixing, cool to at least 45° C.

B. Add methyl paraben and propyl paraben to the mixture from Step A and continue mixing until a homogenous blend is obtained.

C. Preblend the cationic derivative of guar gum, mixed Na/Ca salt of methyl vinyl ether-maleic anhydride, sodium carboxymethylcellulose and ethylene oxide polymer; add to the above mixture with continued mixing. After about 5 minutes scrape down as needed. Reduce pressure to about 28-29 inches vacuum and mix for about 5-10 additional minutes. The product is removed and stored for use.

The mixture prepared according to the aforementioned procedure when hydrated provided excellent adhesive and cohesive characteristics.

EXAMPLE 2

Preparation of a Denture Adhesive Cream

A denture adhesive cream was prepared according to the procedure of Example 1, using the following ingredients:

| Ingredients | Percent W/W |
| --- | --- |
| Mineral oil | 21.5 |
| Petrolatum | 22.5 |
| Fumed silica | 1.00 |
| Mixed Na/Ca salt of methyl vinyl ether-maleic anhydride | 27.00 |
| Sodium carboxymethylcellulose | 13.00 |
| Cationic derivative of guar gum | 13.00 |
| Ethylene oxide polymer | 1.85 |
| Methyl paraben | 0.05 |
| Propyl paraben | 0.10 |
| | 100.00 |

The mixture of this example when hydrated set up to form a cohesive, non-oozing denture adhesive exhibiting excellent denture holding and adhesive duration properties.

The invention being thus described, it will be obvious that the same may be varied in many ways. Such variations are not to be regarded as a departure from the spirit and scope of the invention and all such modifications are intended to be included within the scope of the following claims.

What is claimed is:

1. A denture adhesive base composition comprising a substantially anhydrous mixture of from about 12.5 to about 50 percent by weight, based on the total weight of the denture adhesive base composition, of a cationic derivative of guar gum that comprises guar gum, 2-hydroxy-3-(trimethyl ammonio)-propyl ether, chloride, from about 33 to about 75 percent by weight, based on the total weight of the denture adhesive base composition, of a mixed Na/Ca salt of methyl vinyl ether-maleic anhydride, and from about 12.5 to about 62 percent by weight, based on the total weight of the denture adhesive base composition, of sodium carboxymethylcellulose.

2. The denture adhesive base composition of claim 1, wherein said cationic derivative of guar gum is present in amounts of from about 17 to about 27 percent by weight, based on the total weight of the denture adhesive base composition, said mixed Na/Ca salt of methyl vinyl ether-maleic anhydride is present in amounts of from about 43 to about 53 percent by weight, based on the total weight of the denture adhesive base composition, and said sodium carboxymethylcellulose is present in amounts of from about 17 to about 27 percent by weight, based on the total weight of the denture adhesive base composition.

3. The denture adhesive base composition of claim 1, further including at least one cream base material selected from the group consisting of petrolatum, natural and synthetic oils and mixtures thereof.

4. The denture adhesive base composition of claim 1, further including a cream base material which is a combination of mineral oil with a minor amount of a polyethylene wax having an average molecular weight of 1,000 to 20,000.

5. The denture adhesive base composition of claim 1, further including non-toxic, powdered, excipient materials.

6. The denture adhesive base composition of claim 1, wherein said cationic derivative of guar gum comprises guar gum, 2-hydroxy-3-(Trimethyl ammonio)-propyl ether, chloride.

7. A denture adhesive composition which comprises a substantially anhydrous mixture of from about 40 to about 60 percent by weight, based on the total weight of the denture adhesive composition, of a denture adhesive base composition containing a cationic derivative of guar gum that comprises guar gum, 2-hydroxy-3-(trimethyl ammonio)-propyl ether, chloride, a mixed Na/Ca salt of methyl vinyl ether-maleic anhydride, and sodium carboxymethylcellulose.

8. The denture adhesive composition of claim 7, further including at least one crease base material selected from the group consisting of petrolatum, natural and synthetic oils and mixtures thereof.

9. The denture adhesive composition of claim 7, further including a cream base material which is a combination of mineral oil with a minor amount of a polyethylene wax having an average molecular weight of 1,000 to 20,000.

10. The denture adhesive composition of claim 7, further including non-toxic, powdered, excipient materials.

11. A denture adhesive composition comprising a substantially anhydrous mixture of:
   a) from about 40 to about 60 percent by weight, based on the total weight of the denture adhesive composition, of a denture adhesive base composition containing a cationic derivative of guar gum that comprises guar gum, 2-hydroxy-3-(trimethyl ammonio)-propyl ether, chloride, a mixed Na/Ca salt of methyl vinyl ether-maleic anhydride, and sodium carboxymethylcellulose; and
   b) from about 40 to about 60 percent by weight, based on the total weight of the denture adhesive composition, of additional materials selected from the group consisting of waxes, oils, preservatives, flavoring agents, colorants, sweetening agents, viscosity modifiers, and mixtures thereof.

12. A denture adhesive composition comprising a substantially anhydrous mixture of:
   a) from about 10 to about 20 percent by weight, based on the total weight of the denture adhesive composition, of a cationic derivative of guar gum that comprises guar gum, 2-hydroxy-3-(trimethyl ammonio)-propyl ether, chloride;
   b) from about 20 to about 30 percent by weight, based on the total weight of the denture adhesive composition, of a mixed Na/Ca salt of methyl vinyl ether-maleic anhydride;
   c) from about 10 to about 25 percent by weight, based on the total weight of the denture adhesive composition, of sodium carboxymethylcellulose; and
   d) additional materials in an amount sufficient to yield a denture adhesive composition having a total weight equal to 100 percent by weight of the total denture adhesive composition.

13. The denture adhesive composition of claim 12, wherein said additional materials are selected from the group consisting of waxes, oil, preservatives, flavoring agents, colorants, sweetening agents, viscosity modifiers and mixtures thereof.

14. A method for preparing a denture adhesive base composition comprising:
   a) preparing a substantially anhydrous mixture of from about 12.5 to about 50 percent by weight, based on the total weight of the denture adhesive base composition, of a cationic derivative of guar gum that comprises guar gum, 2-hydroxy-3-(trimethyl ammonio)-propyl ether, chloride, from about 33 to about 75 percent by weight, based on the total weight of the denture adhesive base composition, of a mixed Na/Ca salt of methyl vinyl ether-maleic anhydride, and from about 12.5 to about 62 percent by weight, based on the total weight of the denture adhesive base composition, of sodium carboxymethylcellulose;
   b) forming a denture adhesive base composition including said mixture; and
   c) recovering said denture adhesive base composition.

15. The method of claim 14, wherein said cationic derivative of guar gum is present in amounts of from about 17 to about 27 percent by weight, based on the total weight of the denture adhesive base composition, said mixed Na/Ca salt of methyl vinyl ether-maleic anhydride is present in amounts of from about 43 to about 53 percent by weight, based on the total weight of the denture adhesive base composition, and said sodium carboxymethylcellulose is present in amounts of from about 17 to about 27 percent by weight, based on the total weight of the denture adhesive base composition.

16. The method of claim 14, wherein said denture adhesive base composition further includes at least one cream base material selected from the group consisting of petrolatum, natural and synthetic oils and mixtures thereof.

17. The method of claim 14, wherein said denture adhesive base composition further includes a cream base material which is a combination of mineral oil with a minor amount of a polyethylene wax having an average molecular weight of 1,000 to 20,000.

18. The method of claim 14, wherein said denture adhesive base composition further includes non-toxic, powdered, excipient materials.

19. A method for preparing a denture adhesive composition comprising:
   a) preparing a substantially anhydrous mixture of from about 40 to about 60 percent by weight, based on the total weight of the denture adhesive composition, of a denture adhesive base composition containing a cationic derivative of guar gum that comprises guar gum, 2-hydroxy-3-(trimethyl ammonio)-propyl ether, chloride, a mixed Na/Ca salt of methyl vinyl ether-maleic anhydride, and sodium carboxymethylcellulose;
   b) mixing the denture adhesive base with from about 40 to about 60 percent by weight, based on the total weight of the denture adhesive composition, of additional materials selected from the group consisting of waxes, oils, preservatives, flavoring agents, colorants, sweetening agents, viscosity modifiers, and mixtures thereof;
   c) forming a denture adhesive composition including said denture adhesive base composition; and
   d) recovering said denture adhesive composition.

20. The method of claim 19, wherein said denture adhesive composition further includes at least one cream base material selected from the group consisting of petrolatum, natural and synthetic oils and mixtures thereof.

21. The method of claim 19, wherein said denture adhesive composition further includes a cream base material which is a combination of mineral oil with a minor amount of a polyethylene wax having an average molecular weight of 1,000 to 20,000.

22. The method of claim 19, wherein said denture adhesive composition further includes non-toxic, powdered, excipient materials.

23. A method for preparing a denture adhesive composition comprising:
   a) preparing a substantially anhydrous mixture of:
      i) from about 40 to about 60 percent by weight, based on the total weight of the denture adhesive composition, of a denture adhesive base composition containing a cationic derivative of guar gum that comprises guar gum, 2-hydroxy-3-(trimethyl ammonio)-propyl ether, chloride, a mixed Na/Ca salt of methyl vinyl ether-maleic anhydride, and sodium carboxymethylcellulose;
      ii) from about 40 to about 60 percent by weight, based on the total weight of the denture adhesive composition, of additional materials selected from the group consisting of waxes, oils, preservatives, flavoring agent, colorants, sweetening agents, viscosity modifiers, and mixtures thereof;
   b) forming a denture adhesive composition including said mixture; and
   c) recovering said denture adhesive composition.

24. A method for preparing a denture adhesive composition comprising:
   a) preparing a substantially anhydrous mixture of:
      i) from about 10 to about 20 percent by weight, based on the total weight of the denture adhesive composition, of a cationic derivative of guar gum that comprises guar gum, 2-hydroxy-3-(trimethyl ammonio)-propyl ether, chloride;
      ii) from about 20 to about 30 percent by weight, based on the total weight of the denture adhesive composition, of a mixed Na/Ca salt of methyl vinyl ether-maleic anhydride;
      iii) from about 10 to about 25 percent by weight, based on the total weight of the denture adhesive composition, of sodium carboxymethylcellulose; and
      iv) additional materials in an amount sufficient to yield a denture adhesive composition having a total weight equal to 100 percent by weight of the total denture adhesive composition;
   b) forming a denture adhesive composition including said mixture; and
   c) recovering said denture adhesive composition.

25. The method of claim 24 wherein said additional materials are selected from the group consisting of waxes, oils, preservatives, flavoring agents, colorants, sweetening agents, viscosity modifiers and mixtures thereof.

* * * * *